United States Patent
Nagaiwa et al.

(10) Patent No.: US 6,303,027 B1
(45) Date of Patent: Oct. 16, 2001

(54) APPARATUS FOR CONTROLLING QUALITY OF TREATED WATER

(75) Inventors: Akihiro Nagaiwa; Osamu Yamanaka; Masahiko Tsutsumi; Yasuhiko Nagamori, all of Fuchu; Yukio Hatsushika, Ebina; Masajiro Nakada, Tokyo-to; Kazuhiro Horie, Fuchu; Masaki Kunimi, Hoya; Tetsuya Shinohara, Kobe; Hiroshi Yuuki, Kunitachi, all of (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/513,082

(22) Filed: Feb. 25, 2000

(30) Foreign Application Priority Data

Feb. 26, 1999 (JP) .................................................. 11-051257

(51) Int. Cl.$^7$ .................................................. B01D 17/12
(52) U.S. Cl. .......................... 210/143; 210/97; 210/614; 706/21; 706/23
(58) Field of Search ................................ 210/85, 87, 94, 210/96.1, 103, 138, 143, 614, 739, 97; 706/16, 21, 23, 903; 700/266, 271, 273, 275; 701/45, 50

(56) References Cited

U.S. PATENT DOCUMENTS 5,547,578 * 8/1996 Nielsen ................................ 210/614
5,589,068 * 12/1996 Nielsen ................................ 210/614
5,774,633 * 6/1998 Baba et al. .
5,852,817 * 12/1998 Kano ..................................... 706/23

OTHER PUBLICATIONS

Publication Article "Micro–controller System for Water and Sewage Works", published in Fuji Electric Rev., vol. 24, NOI. 1 , 1978 by Yuki Ito , NOboru Satake, MichinosukeKono and Narumi Ibe, 1978.*

* cited by examiner

Primary Examiner—Joseph W. Drodge
(74) Attorney, Agent, or Firm—Oblon, Spivak, McClelland, Maier & Neustadt, P.C.

(57) ABSTRACT

A treated water quality control system (10) has a sewage inflow estimating unit (1) for estimating an inflow of sewage and a process data storage unit (3) for storing process data on a sewage treatment plant (50). An estimated sewage inflow estimated by the sewage inflow estimating unit (1) and process data read from the process data storage unit (3) are given to a manipulated variable calculating unit (20). The manipulated variable calculating unit (20) calculates values of manipulated variables to be used by a process controller (6) for controlling the sewage treatment plant (50). The values of the manipulated variables calculated by the manipulated variable calculating unit (20) and the process data read from the process data storage unit (3) are given to a process condition estimating arithmetic unit (21). Data on estimated process conditions estimated by the process condition estimating arithmetic unit (21) is given to the manipulated variable calculating unit (20), and then the manipulated variable calculating unit (20) calculates values of the manipulated variables again.

8 Claims, 3 Drawing Sheets

APPARATUS FOR CONTROLLING QUALITY OF TREATED WATER

TECHNICAL FIELD

The present invention relates to a treated water quality control system for controlling the quality of treated water obtained by treating sewage by a sewage treatment plant.

BACKGROUND ART

For example, when controlling the flow rate of aeration air supplied to an aeration tank to promote biological reaction in a sewage treatment plant provided with a biological reaction tank, a flow rate control method controls the flow rate of aeration air in proportion to the inflow of sewage. However, reaction rate is dependent on the quality of water and hence the feed forward flow rate control method is unable to control the flow rate properly and to reduce the cost.

In another treatment process, such as a returned sludge quantity control, processes are controlled individually. However, the control of the general operation of the sewage treatment plant for the stabilization of water quality and the reduction of processing costs has not been conducted.

The improvement of the quality of treated water (observation of standards) is desired for the maintenance of environmental water condition. However, the currently used control method requires much water disposal costs and it has been desired to control water quality capable of reducing treatment costs, maintaining satisfactory water quality. The general operation and control of a water sewage treatment plant have been desired.

However, as mentioned previously, any control for stabilizing water quality and reducing treatment costs has not been achieved.

DISCLOSURE OF THE INVENTION

The present invention has been made in view of such problems and it is therefore an object of the present invention to provide a treated water quality control system for controlling the quality of treated water capable of stabilizing the quality of treated water and of reducing treatment costs.

According to the present invention, a treated water quality control system for controlling the quality of treated water obtained by treating sewage by a sewage treatment plant comprises: a sewage inflow estimating unit for estimating an inflow of sewage; a process data storage unit for storing process data on the sewage treatment plant; a process controller for controlling devices included in the sewage treatment plant; a manipulated variable calculating unit for calculating manipulated variables for controlling the process controller on the basis of the inflow of sewage estimated by the sewage inflow estimating unit and the process data read from the process data storage unit; and a process condition estimating arithmetic unit for estimating the conditions of the sewage treatment plant on the basis of the process data read from the process data storage unit and for making the manipulated variable calculating unit update the calculated manipulated variables and determine optimum values of manipulated variables.

According to the present invention, a treated water quality control system for controlling quality of treated water obtained by treating sewage by a sewage treatment plant comprises: a sewage inflow estimating unit for estimating an inflow of sewage; a process data storage unit for storing process data on the sewage treatment plant; an operation result data storage unit for storing operation result data of past operations of the sewage treatment plant; a process controller for controlling devices included in the sewage treatment plant; a day condition input unit for inputting conditions of weather and atmospheric temperature of the day; an analogous operating condition data retrieving unit for retrieving operation result data on a past analogous operating day on the basis of the inflow of the sewage estimated by the sewage inflow estimating unit, the conditions of weather and atmospheric temperature of the day provided by the day condition input unit and the operation result data of the past operations provided by the operation result data storage unit; and a process condition estimating arithmetic unit for estimating process conditions of the sewage treatment plant on the basis of the operation result data on the past analogous day provided by the analogous operating condition retrieving unit and the process data read from the process data storage unit.

According to the present invention, a treated water quality control system for controlling the quality of treated water obtained by treating sewage by a sewage treatment plant comprises: a sewage inflow estimating unit for estimating an inflow of sewage; a process data storage unit for storing process data on the sewage treatment plant; an operation result data storage unit for storing operation result data of past operations of the sewage treatment plant; a process controller for controlling devices included in the sewage treatment plant; an operating condition specifying unit for specifying operating conditions on an optionally set day on the basis of the operation result data read from the operation result data storage unit; and a process condition estimating arithmetic unit for estimating process conditions of the sewage treatment plant on the basis of the operating conditions for the set day specified by the operation data specifying unit and the process data read from the process data storage unit.

The present invention stabilizes the quality of treated water with reliability.

BEST MODE FOR CARRYING OUT THE INVENTION

Figure 1:
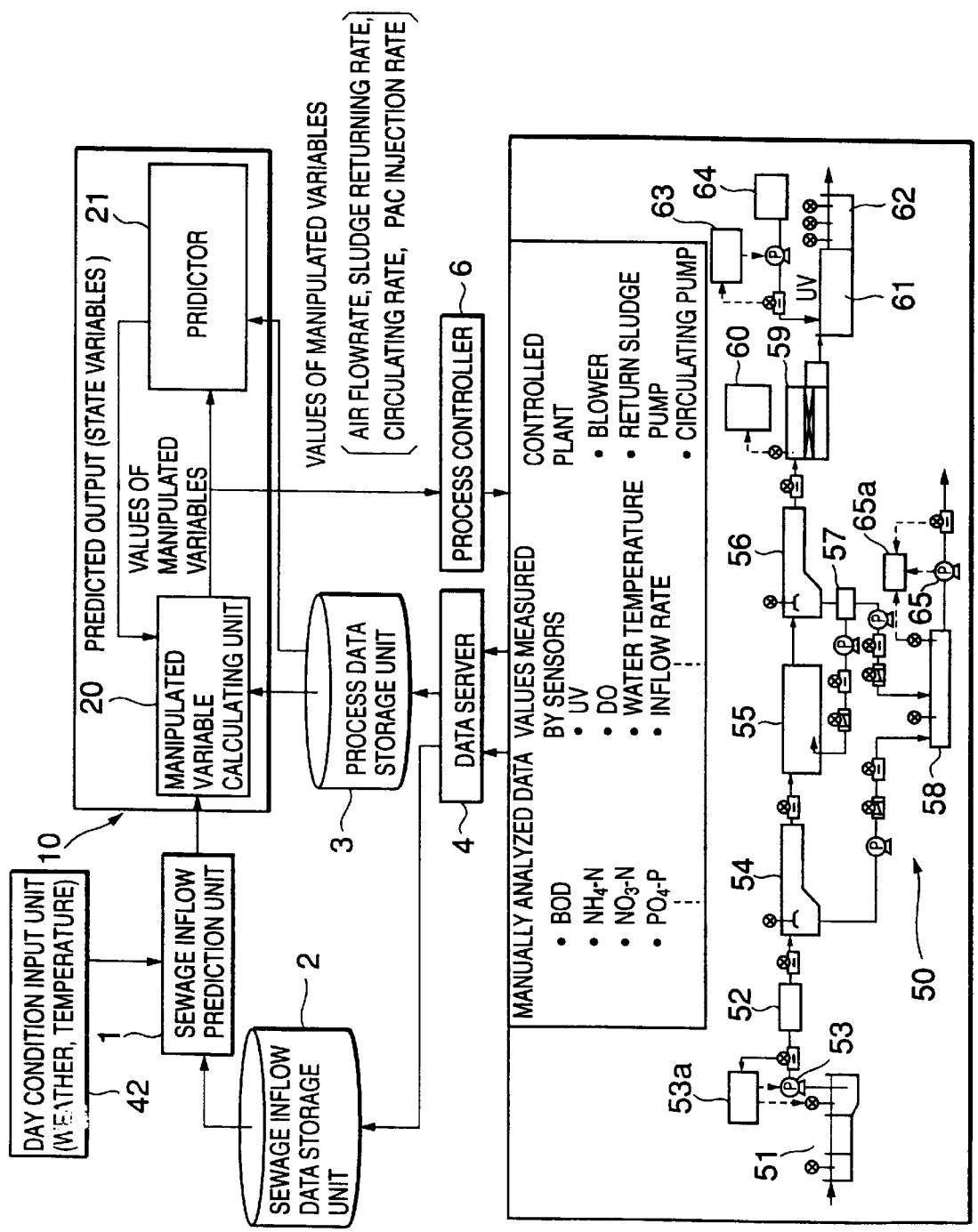
FIG. 1 is a block diagram of a treated water quality control system in a first embodiment according to the present invention.

Preferred embodiments of the present invention will be described hereinafter with reference to the accompanying drawings. FIG. 1 is a block diagram of a treated water quality control system in a first embodiment according to the present invention.

Referring to FIG. 1, a sewage treatment plant 50 includes a sand basin 51 for receiving sewage and removing sand and large matters from the sewage, a solid-removed sewage receiving basin 52 for receiving the sewage from the sand basin 51, and a pump 53 installed between the sand basin 51 and the solid-removed sewage receiving basin 52 and controlled by a pump controller 53a.

The solid-removed sewage received in the solid-removed sewage receiving basin 52 is treated while the same flows through an initial sedimentation basin 54, a biological reaction tank 55 and a final sedimentation basin 56 in that order. Treated water thus obtained by treating the sewage is sent to a sand filtration tank 59.

Subsequently, the treated water is sent to a dis infecting plant 61, where chlorine is added to the treated water. The disinfected treated water is discharged through a discharge conduit 62.

Meanwhile, sludge accumulated in the final sedimentation basin 56 is transferred to a sludge pit 57, and then the sludge is returned to the biological reaction tank 55. Surplus sludge is sent from the sludge pit 57 to a surplus sludge tank 58. The surplus sludge is sent together with sludge sent from the initial sedimentation basin 54 to the surplus sludge tank 58 to a sludge disposal plant by a pump 65 controlled by a sludge controller 65a.

A treated water quality control system 10 includes a sewage inflow data storage unit 2 for storing data on past sewage inflow, a day condition input unit 42 for inputting data representing current conditions, such as those of weather and temperature of the day, and a sewage inflow estimating unit (sewage inflow prediction unit) 1 for estimating (predicting) a sewage inflow for every hour ($m^3/h$) in the day (24 h).

The sewage treatment plant 50 sends process data (data representing the current process conditions) through a data server 4 to a process data storage unit 3. The sewage inflow estimating unit 1 and the process data storage unit 3 are connected to a manipulated variable calculating unit 20. The manipulated variable calculating unit 20 provides values of manipulated valuables for a process controller 6. The manipulated variable calculating unit 20 and the process data storage unit 3 are connected to a process condition estimating arithmetic unit (predictor) 21 capable of water quality simulation. The process condition estimating arithmetic unit 21 carries out operations to estimate the process conditions of the sewage treatment plant 50 by using a biological reaction model, the values of manipulated variables provided by the manipulated variable calculating unit 20 and the process data read from the process data storage unit 3. The biological reaction model used by the process condition estimating arithmetic unit 21 is Model No. 2 specified by IAWQ.

The data calculated by the process condition estimating arithmetic unit 21 is given to the manipulated variable calculating unit 20 and the manipulated variable calculating unit 20 performs calculation again to obtain optimum values of the manipulated variables. The optimum values of the manipulated variables are given to the process controller 6, and the process controller 6 controls the flow rate of air supplied to the biological reaction tank 55, the amount the sludge returned from the sludge pit 57 to the biological reaction tank 55 and the like.

The operation of this embodiment thus constituted will be described hereinafter.

The sewage inflow estimating unit 1 estimates a sewage inflow for the day on the basis of data on past sewage inflow and data representing the weather and temperature of the day entered by operating the day condition input unit 42. The sewage inflow for the day estimated by the sewage inflow estimating unit 1 and current process data read from the process data storage unit 3 are given to the manipulated variable calculating unit 20. The manipulated variable calculating unit 20 calculates values of the manipulated variables to be used by the process controller 6 for control operations. The process data read from the process data storage unit 3 and the values of manipulated variables calculated by the manipulated variable calculating unit 20 are given to the process condition estimating arithmetic unit 21.

Meanwhile, the manipulated variable calculating unit 20 calculates the values of the manipulated variables by using a linear model representing a simplified complicated biological reaction processes on the basis of the estimated sewage inflow estimated by the sewage inflow estimating unit 1 and the current process data read from the process data storage unit.

The process condition estimating arithmetic unit 21 carries out operations using the rigorous biological reaction model (Model No. 2, IAWQ) to estimate (predict) data representing process state variables (data indicating a changing state of water quality) and gives the data on the estimated condition to the manipulated variable calculating unit 20. The manipulated variable calculating unit 20 calculates again values of the manipulated variables to update the values of the manipulated variables. Thus, the manipulated variable calculating unit 20 repeats calculations to provide optimum values of the manipulated variables.

Then, the process controller 6 carries out control operations on the basis of the optimum values of the manipulated variables calculated by the manipulated variable calculating unit 20. The components of the sewage treatment plant 50 are controlled by the process controller 6 to make the sewage treatment plant 50 produce treated water of stable water quality.

A treated water quality control system in a second embodiment according to the present invention will be described with reference to FIG. 2. The treated water quality control system in the second embodiment shown in FIG. 2 has a manipulated variable calculating unit 20. When calculating optimum values of manipulated variables, the manipulated variable calculating unit 20 uses information provided by a performance function storage unit 22, a constraint storage unit 23 and a sewage quality estimating unit (sewage quality prediction unit) 31. The second embodiment is substantially the same as the first embodiment shown in FIG. 1 in other respects.

Figure 2:
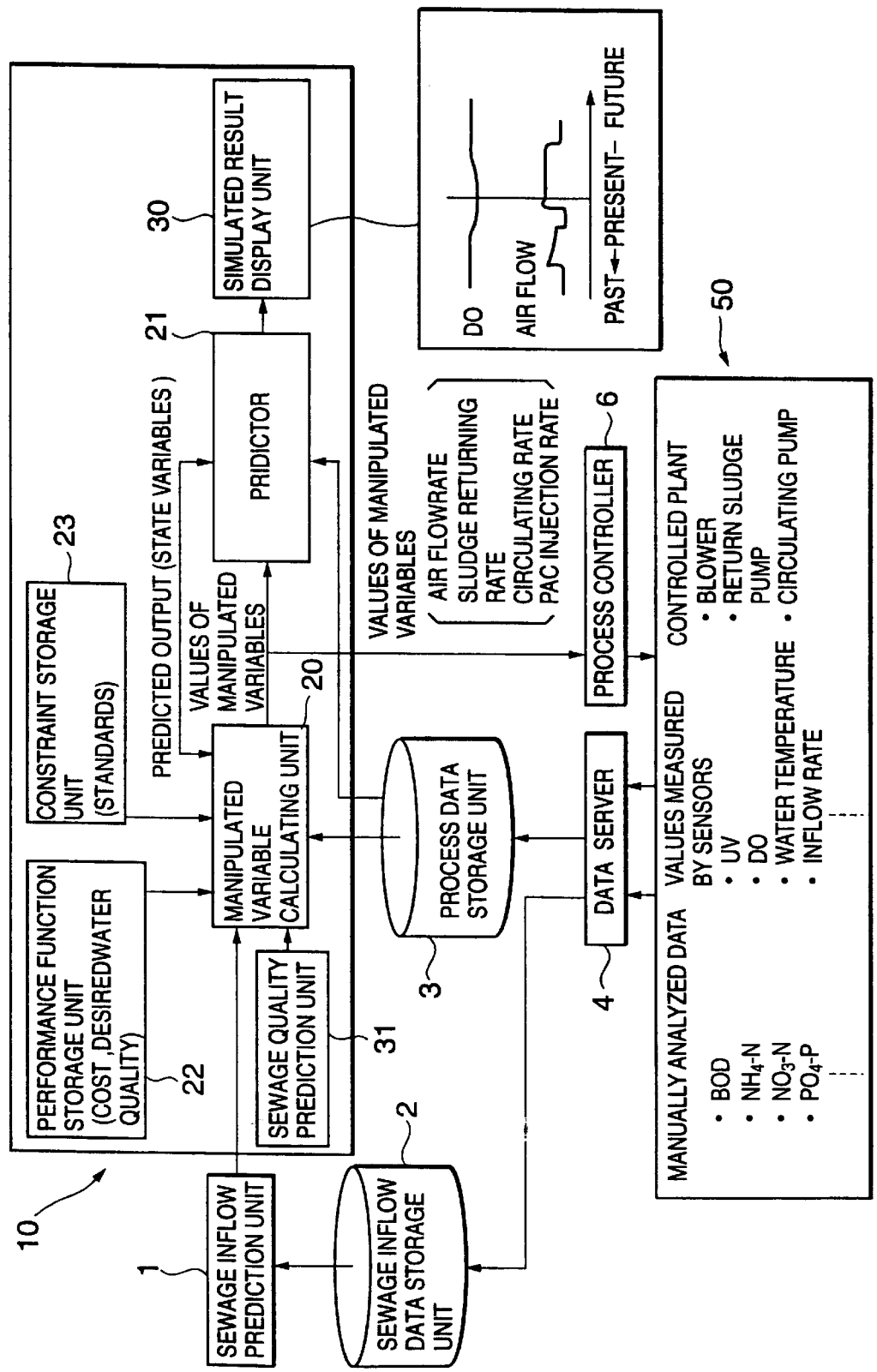
FIG. 2 is a block diagram of a treated water quality control system in a second embodiment according to the present invention.

In FIG. 2, parts like or corresponding to those of the first embodiment are denoted by the same reference characters and the description thereof will be omitted.

Referring to FIG. 2, the performance function storage unit 22 stores a performance function to reduce operating cost to the least extent and to optimize process conditions so that the quality of treated water is as close as possible to a desired water quality. The constraint storage unit 23 stores constraints to be fulfilled to satisfy water quality standards.

The performance function and the constraints will be described hereinafter.

Performance function: $W_1 \cdot J_1$ (cost)+$W_2 \cdot J_2$ (desired water quality)

$J_1$=(Unit price of power)×{(Rated power of blower×quantity of air)+(Rated power of sludge returning pump)×(Amount of returned sludge)}

$J_2 = (T \cdot N - T \cdot N^*)^2 + (T \cdot P - T \cdot P^*)^2$ where $W_1$, $W_2$: Weighting factors, T·N: Total amount of nitrogen T·N*: Desired total amount of nitrogen T·P: Total amount of phosphorus T·P*: Desired total amount of phosphorus Constraint, Water quality standards:

T·N<10, T·P<1

The manipulated variable calculating unit 20 is able to calculate optimum values of the manipulated variables by solving a nonlinear optimization problem defined by the performance function and the foregoing restraints by using, for example, a quadratic programming method, i.e., one of methods of solving a nonlinear optimization problem.

Optimum conditions for operations in one day can be determined, for example, by deciding restraints on operations in every hour for 24 h and calculating the performance function for 24 h. The manipulated variable calculating unit 20 may use data on an estimated sewage quality provided by the sewage quality estimating unit 31 in addition to input data for calculating values of the manipulated variables.

As shown in FIG. 2, a simulated result displaying unit 30 may be connected to the process condition estimating arithmetic unit 21 to display data on estimated future process conditions.

A treated water quality control system in a third embodiment according to the present invention will be described with reference to FIG. 3. In the third embodiment, a process condition estimating arithmetic unit 21 estimates process conditions on the basis of operation result data of past operations.

Figure 3:
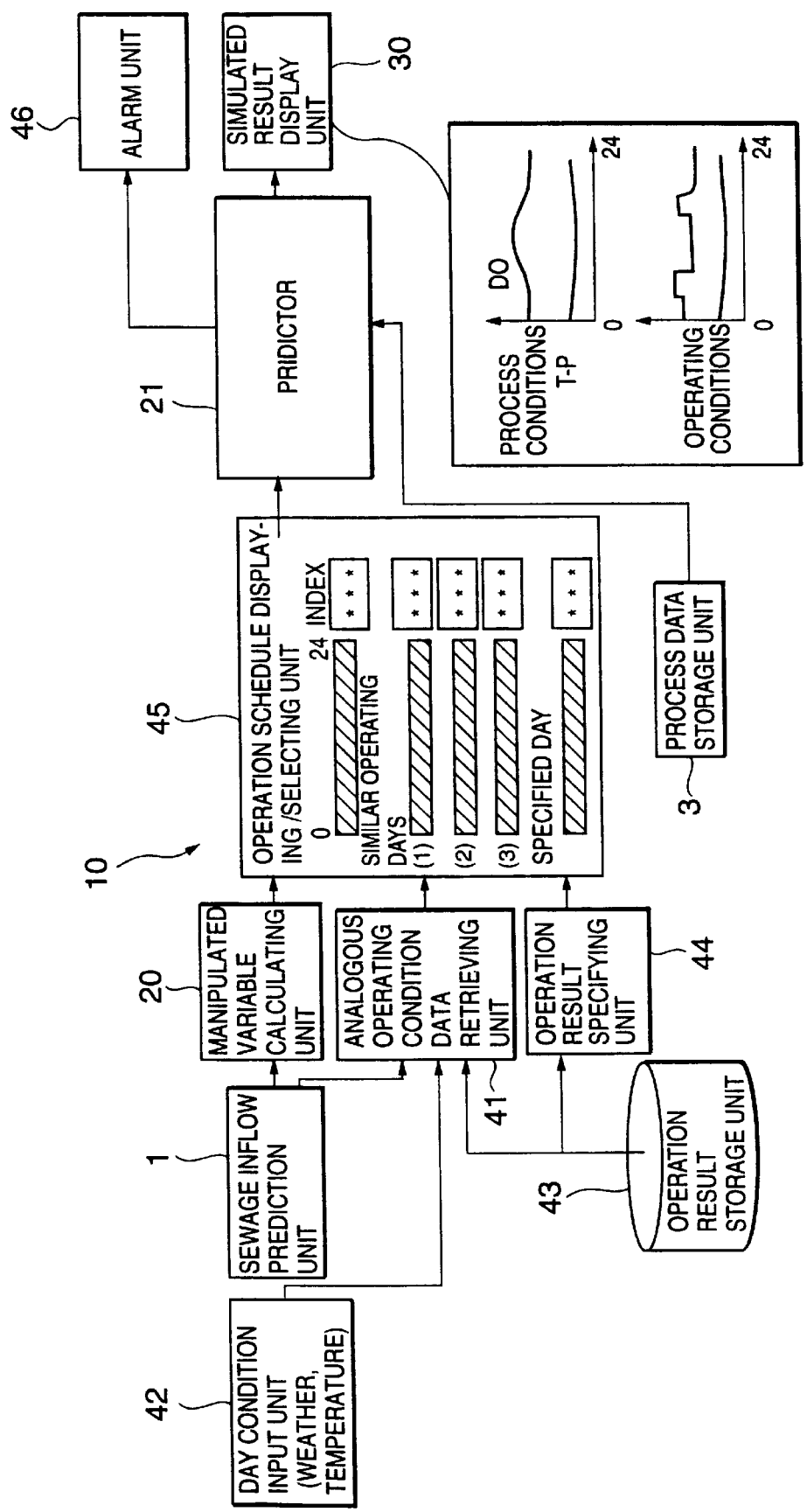
FIG. 3 is a block diagram of a treated water quality control system in a third embodiment according to the present invention.

Referring to FIG. 3, an analogous operating condition data retrieving unit 41 operates on the basis of day condition data entered by a day condition input unit 42, such as data on the weather and temperature of the operating day, retrieves automatically the operation result data of operation on a past analogous operating day (similar operating day), and determines operating conditions for the operating day on the basis of the results of operation on the past analogous operating day.

Operating conditions for the operating day may be determined on the basis of the operation result data on an optionally set operating day read from an operation result data storage unit 43. The optional set operating day is set by an operation result specifying unit 44.

An operation schedule displaying/selecting unit 45 selects operating conditions for the day from a plurality of operating conditions provided by the analogous operating condition data retrieving unit 41 and the operation result specifying unit 44.

The operation schedule displaying/selecting unit 45 displays operation costs (amount of power necessary for operations) and the performance function explained in connection with the second embodiment as indices of selection to facilitate selection. A signal provided by the manipulated variable calculating unit 20 is given to the operation schedule displaying/selecting unit 45.

The process condition estimating arithmetic unit (predictor) 21 estimates estimated process conditions when operations selected by the operation schedule displaying/selecting unit 45 are executed on the basis of operation data provided by the operation schedule displaying/selecting unit 45 and process data read from the process data storage unit. the estimated data is displayed by the simulated result displaying unit 30.

If it is expected that an abnormal condition will occur in the process from process simulation carried out by the process condition estimating arithmetic unit 21, an alarm unit 46 gives an alarm that an abnormal condition will occur, so that measures can be taken beforehand to prevent the abnormal condition.

In the foregoing embodiment, the manipulated value calculating unit 20 may calculate the values of the manipulated variables for every hour in 24 h, for example, once a day by changing the time for control and the period of calculation or the values of the manipulated variables may be calculated every 10 min, for example, to time two hours after the present time. Thus, long-time control and long-time guidance, or short-time control and short-time guidance may be performed.

Although the control system has been described as applied to the control of the sewage disposal processes, the control system is. applicable to other water treatment processes.

As is apparent from the foregoing description, according to the present invention, when controlling a sewage treatment plant, the quality of the treated water can be improved (observation of standards), efficient operation that reduces disposal cost can be achieved. The general operations of the disposal plant can be achieved.

What is claimed is:

1. A treated water quality control system for controlling a quality of treated water obtained by treating sewage by a sewage treatment plant, said treated water quality control system comprising:

a sewage inflow estimating unit configured to estimate an inflow of sewage;

a process data storage unit configured to store process data on the sewage treatment plant;

a process controller configured to control devices included in the sewage treatment plant;

a manipulated variable calculating unit configured to calculate manipulated variables for controlling the process controller on the basis of the inflow of sewage estimated by the sewage inflow estimating unit and the process data read from the process data storage unit; and a process condition estimating arithmetic unit configured to predict future process conditions of the sewage treatment plant on the basis of process data read from the process data storage unit and the manipulated variables calculated by the manipulated variable calculating unit and configured to make the manipulated variable calculating unit update the calculated manipulated variables and determine optimum values of manipulated variables.

2. The treated water quality control system according to claim 1, wherein the manipulated variable calculating unit determines optimum values of the manipulated variables by using a performance function for reducing operation cost to a minimum and making the quality of the treated water approach a desired value, and constraints to be fulfilled to satisfy water quality standards.

3. The treated water quality control system according to claim 1, wherein the manipulated variable calculating unit calculates the manipulated variables by using a linear model representing a simplified biological reaction process.

4. The treated water quality control system according to claim 1, wherein the process condition estimating arithmetic unit estimates the process conditions by calculation using a biological reaction model.

5. A treated water quality control system for controlling a quality of treated water obtained by treating sewage by a sewage treatment plant, said treated water quality control system comprising:

a sewage inflow estimating unit configured to estimate an inflow of sewage;

a process data storage unit configured to store process data on the sewage treatment plant;

an operation result data storage unit configured to store operation result data of past operations of the sewage treatment plant;

a process controller configured to control devices included in the sewage treatment plant;

a day condition input unit configured to input current weather conditions of a day;

an analogous operating condition data retrieving unit configured to retrieve operation result data on a past analogous operating day on the basis of the inflow of the sewage estimated by the sewage inflow estimating unit, the current weather conditions of the day input by the day condition input unit and operation result data of the past operations provided by the operation result data storage unit;

a process condition estimating arithmetic unit configured to predict future process conditions of the sewage treatment plant on the basis of the operation result data on the past analogous day provided by the analogous operating condition retrieving unit and the process data read from the process data storage unit.

6. The treated water quality control system according to claim 5 further comprising:

a display unit configured to display results of simulation, connected to the process condition estimating arithmetic unit.

7. A treated water quality control system for controlling a quality of treated water obtained by treating sewage by a sewage treatment plant, said treated water quality control system comprising:

a sewage inflow estimating unit configured to estimate an inflow of sewage;

a process data storage unit configured to store process data on the sewage treatment plant;

an operation result data storage unit configured to store operation result data of past operations of the sewage treatment plant;

a process controller configured to control devices included in the sewage treatment plant;

an operating condition specifying unit configured to specify operating conditions on an optionally set day on the basis of operation result data read from the operation result data storage unit; and a process condition estimating arithmetic unit configured to predict future process conditions of the sewage treatment plant on the basis of the operating conditions for the set day specified by the operation data specifying unit and process data read from the process data storage unit.

8. The treated water quality control system according to claim 7 further comprising:

a display unit configured to display results of simulation, connected to the process condition estimating arithmetic unit.

* * * * *